United States Patent [19]

Bombeck, IV

[11] Patent Number: 4,981,470
[45] Date of Patent: Jan. 1, 1991

[54] INTRAESOPHAGEAL CATHETER WITH PH SENSOR

[75] Inventor: C. Thomas Bombeck, IV, Irving, Tex.
[73] Assignee: Synectics Medical, Inc., Irving, Tex.
[21] Appl. No.: 371,983
[22] Filed: Jun. 21, 1989
[51] Int. Cl.$^5$ .............................................. A61B 5/05
[52] U.S. Cl. .................................... 128/635; 128/642; 128/780; 606/196
[58] Field of Search .................................. 604/96–98, 604/100; 128/344, 207.14, 207.15, 636, 672, 716, 759, 771, 780, 635, 642, 632

[56] References Cited

U.S. PATENT DOCUMENTS

| | | | |
|---|---|---|---|
| 2,857,915 | 10/1958 | Sheridan | 604/280 |
| 3,373,735 | 3/1968 | Gallagher | 128/771 |
| 3,480,003 | 11/1969 | Crites | 128/780 |
| 3,905,889 | 9/1975 | Macur et al. | 128/635 X |
| 4,471,779 | 9/1984 | Antoshkin et al. | 128/344 |
| 4,503,859 | 3/1985 | Petty et al. | 128/780 |
| 4,600,015 | 7/1986 | Evans et al. | 128/780 |
| 4,632,119 | 12/1986 | Reichstein | 128/636 |
| 4,681,116 | 7/1987 | Settler | 128/635 |
| 4,729,384 | 3/1988 | Bazenet | 604/96 |
| 4,776,347 | 10/1988 | Matthews | 604/100 |
| 4,796,629 | 1/1989 | Greyzel | 128/344 |
| 4,834,101 | 5/1989 | Collison et al. | 128/635 |

FOREIGN PATENT DOCUMENTS 0178028 10/1964 U.S.S.R. ............................ 128/780

OTHER PUBLICATIONS

Oesophageal Multipurpose Monitoring Probe; Baker, A. B. and McLead, C. *Anaesthesia*, 1983, vol. 38, pp. 892–897.

Primary Examiner—John D. Yasko
Assistant Examiner—Adam J. Cermak
Attorney, Agent, or Firm—Stephen C. Glazier

[57] ABSTRACT

An intraesophageal catheter comprising a tubular body, a pH sensor extending through the interior of the tubular body for pH measurement, and a balloon inflation pressure sensor communicating with the interior of the tubular body. The tubular body is comprised of clear polyvinyl chloride material and has a radiopaque stripe extending longitudinally along the tubular body. A plurality of circumferential gradations are marked on the tubular body. The pH sensor has a head portion fastened to the end of the tubular body and a conductor connected to and extending from the head portion to the other end of the tubular body. The head portion is comprised of a polycarbonate material having a smooth surface. The balloon inflation pressure sensor is a balloon that is positioned on the tubular body part from the head portion of the pH sensor. A balloon inflation channel extends through the interior of the tubular body and communicates with the balloon molded to the exterior surface of the tubular body.

3 Claims, 2 Drawing Sheets

INTRAESOPHAGEAL CATHETER WITH PH SENSOR

TECHNICAL FIELD

The present invention relates to intraesophageal catheters. More particularly, the present invention relates to devices that monitor pH and inhalation pressures related to respiration in patients and, specifically, in the study of sleep apnea.

BACKGROUND ART

Catheters are well known in medicine and a wide variety exist for a variety of purposes. Catheters are typically flexible tubes of varying sizes that are inserted into the body. One common application of catheters, for example, is the removal of bodily fluids from the bladder during the time when a patient is incapacitated. As the technology of medicine has expanded, catheters are becoming more widely used for a greater variety of purposes.

Presently, catheters exist that have on their distal end a pH sensor. In these types of catheters, an electrical wire runs inside the catheter to the proximal end of the catheter. When the catheter is inserted into the body, this arrangement permits the electrical sensing of pH (that is, acidity) of the immediate environment of the distal tip. Such pH catheters are presently manufactured by Synectics A.B. of Sweden, and distributed in the U.S. by Synectics Medical, Inc. of 1350 Walnut Hill Road, Irving, Tex.

Catheters also exist that have pressure sensors at the distal tip. When these pressure sensors are inserted into the body, the local pressure around the distal tip of the catheter is able to be measured.

A lumen is a channel inside the catheter that runs the length of the catheter. Multiple lumen catheters are well known. These catheters can function much like multiple catheters with each lumen dedicated to one function. As such, a single catheter with multiple lumens can operate as a multiple function catheter. Since the diameter of the catheter is of critical importance, it becomes very difficult to incorporate a large number of lumens within a single catheter. The restriction of space availability inhibits the ability to incorporate many functions into the catheter.

Several methods are known that attempt to measure the degree of effort a patient is exerting in the attempt to breathe. The degree of effort exerted in the attempt to breathe is otherwise identified as "respiratory effort". Such methods include applying stretch sensitive belts to the outside of the abdomen, or the application of electrodes to the chest. These approaches are cumbersome and inaccurate. The most accurate technique for measuring respiratory effort has been used on a small scale basis. This technique consists of measuring air pressure in the esophagus. An effort to inhale results in an air pressure drop in the esophagus and trachea. An effort to exhale causes an increase in the air pressure in the same area. When no effort to breathe occurs, the air pressure in the esophagus will remain constant.

The prior art in the area of measuring air pressure in the esophagus consists of placing a balloon made from the finger of a latex glove on the end of an esophageal catheter. This balloon is then partially inflated. An air pressure monitor at the proximal end of the catheter connected to the balloon indicates respiratory effort. The relatively large size of the balloon often interfered with the esophageal function and other simultaneous intraesophageal catheterizations.

Soviet Patent No. 272,477, issued on May 20, 1968 to Leya and Berzinsh, teaches a stomach-intestinal probe consisting of multiple antimony electrodes to measure stomach acids and a large inflatable balloon to fix the probe in the esophagus so that fluoroscopy can be used to watch the movement of the stomach. This probe permits simultaneous monitoring of stomach acid and stomach movements. However, the balloon is relatively large and blocks esophagus function so as to break normal sleep patterns. Also, the balloon cannot function as a pressure sensor since it is too large and not connected to an external pressure monitor.

German Patent No. 2,162,656, issued to Wolters and Eckert on June 20, 1973, teaches a stomach acid gage with an electrical pH sensor. Once again, this device does not measure respiratory effort. Similar, one-function stomach acid sensors, are taught by U.S. Pat. No. 4,618,929, issued on Oct. 21, 1986, to Miller et al, and by U.S. Pat. No. 4,176,659, issued on Dec. 4, 1979 to Rolfe.

U.S. Pat. No. 4,503,859, issued on Mar. 12, 1985, to Petty, et al, teaches a device to simultaneously monitor esophageal acid and heart EKG. This device does not measure respiratory effort in any way.

German Patent No. DE 3523987A, issued on Jan. 8, 1987, to Lange, teaches a method to measure stomach function consisting of multiple pH sensors attached to the outside of a balloon on a catheter. The balloon, however, is used only to inflate inside the stomach and thereby distribute the pH sensors against the stomach wall. Normal esophageal function is blocked, pH in the esophagus is not tested, and respiratory effort is not measured.

U.S. Pat. No. 4,681,116, issued on July 21, 1987, to Settler, teaches an antimony electrode used as an esophageal electrode. This uses an epoxy resin as a sealant. This is also a single function device which does not simultaneously monitor respiratory effort.

Sleep apnea is the problem of inadequate breathing while asleep. It can have several causes, with each cause requiring different remedies. Hence, individual treatment of sleep apnea can follow only after study of the causes of sleep apnea in the individual.

One alternate cause of sleep apnea is gastroesophageal reflux (GER). GER is the process by which the subject generates acids in the stomach, which are then passed into the esophagus. These acids can then be aspirated into the lungs, causing a constriction of the trachea and difficulty in breathing. However, GER can also be a result, instead of a cause, of sleep apnea. Difficulty in breathing, caused by other reasons, can lead to increased respiratory effort in compensation. This increased effort can then encourage GER. In effect, this causes a sucking of the gastric acid into the esophagus from the stomach.

Therefore, to determine the cause of an individual case of sleep apnea, and to determine the proper remedy, it is necessary in each individual case to study and sort out the cause and effect relationship of GER and respiratory effort. In practice, this requires the accurate simultaneous measurement of intraesophageal acid and respiratory effort. Specifically, this means the accurate simultaneous measurement of pH in the esophagus and air pressure in the esophagus. It is also important that this should be done in a way that does not disturb normal sleep, and other bed activity. Unfortunately, no techniques have been developed which measure both of these factors simultaneously. As a result, the effective study and remedy of sleep apnea eludes medical science.

It is an object of the present invention to provide a catheter that simultaneously monitors intraesophageal pH and air pressure.

It is another object of the present invention to provide such a catheter that can be utilized without disturbing sleep.

It is a further object of the present invention to provide such a catheter that is compatible with fluoroscopy techniques.

It is still a further object of the present invention to provide an instrument that simultaneously monitors gastric reflux and respiratory effort.

These and other objects and advantages of the present invention will become apparent from a reading of the attached specification and appended claims.

SUMMARY OF THE INVENTION

The present invention is an intraesophageal catheter that comprises a tubular body, a pH sensor, and a balloon inflation pressure sensor. The pH sensor lead extends through the interior of the tubular body and is used for the purpose of detecting acidity within the esophagus. The balloon inflation pressure sensor communicates with the interior of the tubular body. The balloon inflation pressure sensor includes a balloon that is attached to the exterior of the tubular body.

The tubular body is comprised of a clear polyvinyl chloride material. This tubular body has a radiopaque stripe that extends for the length of the tubular body. Specifically, this radiopaque stripe is red and is of a type that can easily be seen under fluoroscopy. This radiopaque stripe runs for the entire length of the catheter. The tubular body also has a plurality of circumferential gradations marked on the tubular body. These circumferential gradations are indicative of distance from one end of the tubular body. The tubular body has an outer diameter of 2.1 millimeters. The catheter has a single lumen which is large enough to accommodate the pH sensor lead and allow air flow to pass therethrough.

The pH sensor comprises a head portion that is fastened to one end of the tubular body and a conductor that is connected to the head portion and extends from the head portion to the other end of the tubular body. The head portion is pH sensitive. This head portion is made of a polycarbonate material. This head portion should have a smooth, rounded surface having no sharp edges. This head portion is ultrasonically bonded to one end of the tubular body.

The conductor is a coated wire having a connector fastened to the end of the conductor opposite the head portion. This coated wire is specifically TEFLON coated and has a diameter of approximately 0.8 millimeters. This coated wire is fitted within the lumen of the catheter.

The balloon inflation pressure sensor comprises a balloon that is molded to the exterior surface of the tubular body and a balloon inflation channel that extends through the interior of the tubular body so as to communicate with the interior of the balloon. The balloon inflation channel communicates with the balloon through a plurality of ports extending through the tubular body. The balloon is comprised of a latex material. The balloon has a length of approximately four centimeters and an inflated outer diameter of 8.4 millimeters. The balloon inflation channel is TEFLON-lined so as to increase resistance to radial deformation and reduce air flow resistance. The balloon inflation channel has a female luer lock at the end opposite the balloon.

Both the pH sensor and the balloon inflation pressure sensor are connectable to monitors exterior of the catheter.

DETAILED DESCRIPTION OF THE INVENTION

Figure 1:
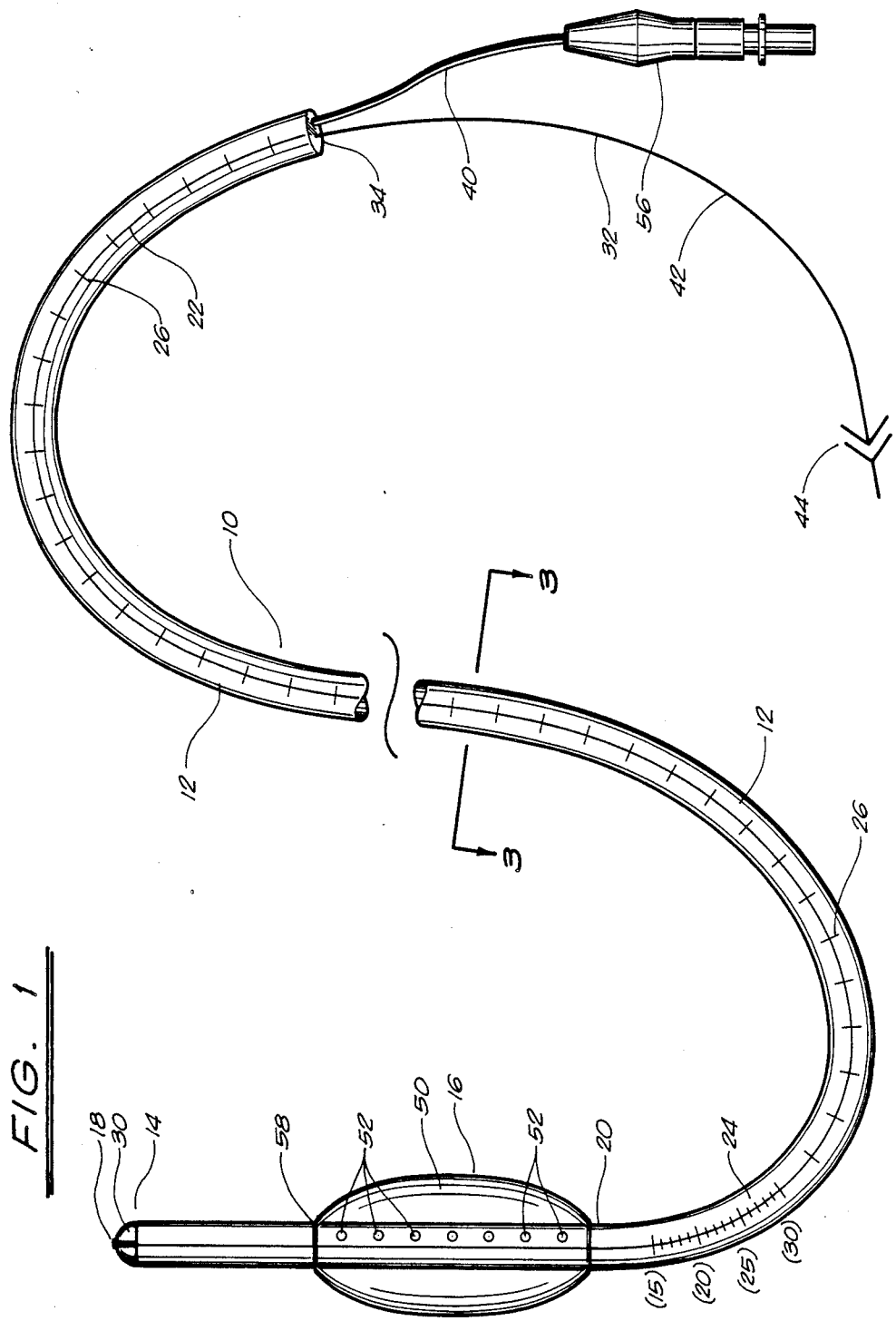
FIG. 1 is a diagrammatic elevational view of the intraesophageal catheter in accordance with the preferred embodiment of the present invention.

FIG. 1 shows the intraesophageal catheter 10 in accordance with the preferred embodiment of the present invention. Intraesophageal catheter 10 comprises tubular body 12, pH sensor 14, and balloon inflation pressure sensor 16. The pH sensor 14 extends through the interior of the tubular body 12 so as to provide for pH measurement at distal end 18. The balloon inflation pressure sensor communicates with the interior of tubular body 12. The balloon inflation measurement sensor 16 is attached to the exterior surface 20 of the tubular body 12 of intraesophageal catheter 10.

Tubular body 12 of catheter 10 is a single lumen catheter having an outer diameter of approximately 2.1 millimeters. The tubular body 12 is comprised of a clear polyvinyl chloride (PVC) material lined in interior with TEFLON. The tubular body 12 includes a red radiopaque stripe 22 extending longitudinally for the entire length of catheter 10. This radiopaque stripe 22 should be of a type that can be easily seen during fluoroscopy.

The tubular body 12 is marked circumferentially with gradations 24. In the preferred embodiment, these gradations occur in one centimeter increments. All of these markings are relative to the distance from the distal tip 18 of catheter 10. Every fifth circumferential mark has a slightly thicker band 26 and is appropriately numbered. The markings and numberings start at the fifteen centimeter mark from the distal tip 18 and proceed approximately to seventy centimeters. These markings allow the user of the catheter 10 to appropriately position the catheter within the body of the patient and to make approximations as to the location of the catheter within the body.

The pH sensor 14 comprises a head portion 30 that is fastened to the distal end of tubular body 12. The pH sensor further comprises a conductor 32 that is connected to the head portion 30 and extends from the head portion 30 to the proximal end 34 of the tubular body. Head portion 30 is of a polycarbonate material having a smooth surface. The pH sensor of the present invention is a Monocrystant Antimony pH sensor. The head portion 30 should be rounded and have no sharp edges. A solvent (THF) may be used for creating a smooth, rounded head portion 30. The head portion 30 should be fixed in place at the end of tubular body 12 by either ultrasonic or vibration bonding. Such ultrasonic or vibration bonding is utilized so that adhesives are not required.

The pH sensor 14 and the balloon inflation pressure sensor 16 should be installed in such a way that the pH sensor 14 and the balloon inflation sensor 16 remain separated. Ideally, this separation should be at least three centimeters. The reason for this separation is to allow the esophagus ample room to contract around the catheter body, distal to the balloon, and clear residual GER away from the pH sensor.

The tubular body 12 should have a length of approximately eighty centimeters. The proximal end 34 of the catheter 10 should be broken out into two clear polyvinyl chloride leads 40 and 42. The pH sensor channel lead 42 should have a length of approximately one hundred and five centimeters and an inner diameter of at least 0.9 millimeters. The pH portion of the catheter 10 will thus have an overall length of one hundred and eighty-five centimeters. The connector between the pH sensor channel and the catheter body 12 and the pH channel lead should have a diameter of at least 0.9 millimeters. The conductor 32 for the pH sensor 14 should be TEFLON coated. This conductor 32 is to be threaded through the pH sensor channel of the catheter 10, through the pH channel lead, and terminated with a male tip plug connector 44. The pH sensor conductor 32 is secured to plug 44. Plug 44 may then be connected to an appropriate monitor for monitoring acidity conditions within the esophagus.

The balloon inflation pressure sensor 16 comprises a balloon 50 that is molded onto the exterior surface 20 of the tubular body 12. In addition, the balloon inflation pressure sensor includes a balloon inflation channel that extends through the interior of the tubular body 12 such that the balloon inflation channel communicates through ports 52 with the interior of the balloon 50. The balloon 50 is comprised of a latex material. This balloon ideally has a length of approximately four centimeters and an inflated outer diameter of 8.4 millimeters. The size of this balloon is specifically selected so as to be of proper size for inflation within the esophageal cavity without causing disturbances of the normal breathing or swallowing process.

As will be described hereinafter, the balloon inflation channel 40 is TEFLON-lined. The balloon inflation channel lead 40 is connected to a plug 56 that may be attached to an adjacent monitor. The balloon channel lead 40 should have a length of 20 centimeters and an inner diameter of approximately 1.2 millimeters. The balloon channel lead 40 should be made of TEFLON and have a cross-sectional configuration such that the lead 40 will not kink. The lead 40 is terminated with a female luer lock 56. The balloon will give an inflated circumference and volume of approximately 26.4 millimeters and three cubic centimeters, respectively. The multiple ports 52 allow the balloon to receive a free and uniform distribution of air. The most distal end of the balloon 58 should be located three centimeters from the distal end 18 of catheter 10. This distance is the most suitable for fitting the balloon in proper position within the esophageal cavity while allowing the head portion 30 to contact the gastric fluids within the esophageal cavity.

Figure 2:
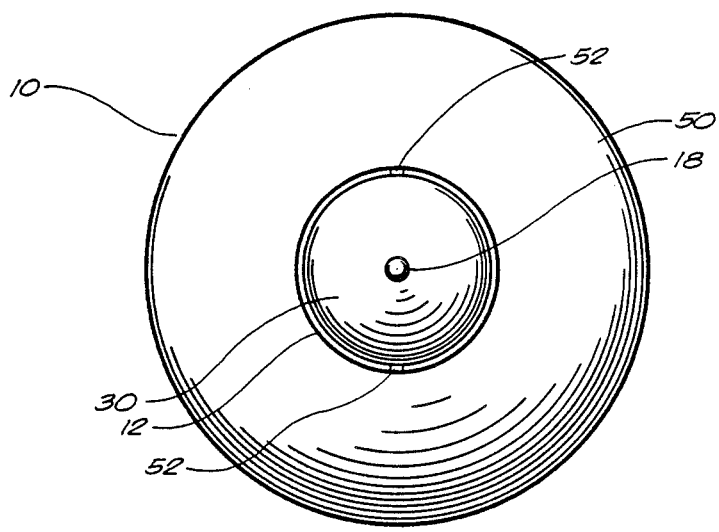
FIG. 2 is an end view of the intraesophageal catheter of the present invention.

Referring to FIG. 2, there is shown an end view of the intraesophageal catheter 10. Specifically, in this end view, there is shown the distal end tip as mounted on head portion 30. The head portion 30 is of a polycarbonate material. The pH sensor conductor is connected to the opposite side (not shown) of this head portion 30. The tubular body 12 receives the head portion 30 by ultrasonic or vibration bonding. Since the instrument of the present invention is to be used in internal medicine, it is important to avoid adhesives and other bonding agents. The balloon 50 is molded onto the surface of tubular body 12. In FIG. 2, the balloon 50 is shown in its expanded condition. Air flows into balloon 50 through special ports 52 opening through distal body 12.

Figure 3:
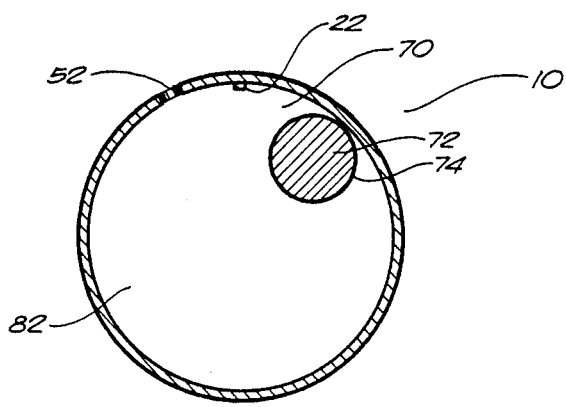
FIG. 3 is a cross-sectional view taken along lines 3—3 of FIG. 1 of the present invention.

FIG. 3 shows the internal configuration of catheter 10. It can be seen that the lumen 70 contains the conductor 72 for the pH sensor 14 (shown in FIG. 1). Conductor 72 is coated with TEFLON material 74. This TEFLON-coated conductor allows the conductor to be easily threaded through the lumen 70 within the catheter 10. This conductor is threaded through the lumen 70 of the catheter 10, through the pH channel lead 42 (as shown in FIG. 1) and eventually terminates with plug 44 (of FIG. 1). The lumen 70 (the pH sensor channel) must be large enough to accommodate the 0.8 millimeter diameter TEFLON coated wire 72 with enough space left over to allow adequate air flow through the lumen 70. The remainder of lumen 70 constitutes the balloon inflation channel 82, which should be TEFLON-lined in order to increase resistance to radial deformation and to reduce air flow resistance. The balloon inflation channel 82 eventually connects with the lead 40 (illustrated in FIG. 1). FIG. 3 also shows the inclusion of the red radiopaque stripe 22 as formed on the clear polyvinyl chloride tubular body 12. FIG. 3 also shows balloon inflation ports 52 passing through catheter wall 12.

In operation, the distal end 18 of the catheter 10 acts as the pH sensor. It electrically communicates with its proximal end through the conductor 72 running the length of the catheter inside lumen 70. This pH sensor functions in the same manner as presently available pH sensors. This distal end 18 allows the sensing of the acidity of the immediate environment of the tip 18.

The balloon 50 is inflated by air communicated through the lumen 80 of the catheter 10. The lumen communicates air into the balloon through ports in the catheter wall that pass directly to the inside of the balloon. The pressure in the balloon 50 is then communicated in a closed pneumatic system to the proximal end 56 of the air lumen 80. The proximal end 56 can then be connected to a suitable measurement and monitoring equipment so as to monitor air pressure.

The present invention also includes a method of measuring the intraesophageal pH and air pressure that comprises the steps of inserting the catheter 10 into the nose of a person and moving the catheter to the bottom of the esophagus. The tip of the catheter should be positioned five centimeters above the lower esophageal sphincter so as to properly detect acidity in such region. The pH measurement lead should then be connected to a monitor exterior of the catheter so as to monitor the condition of the acidity within the esophagus.

The balloon inflation pressure sensor should then be activated by slightly inflating the sensor. The respiratory effort of the person receiving the catheter will be reflected by changes of air pressure within the balloon channel. The proximal end of this channel is then connected to a pressure transducer exterior of the patient. As such, both the pH and the respiratory effort can be measured simultaneously.

In the study of sleep apnea, the present invention allows the measurement and the evaluation of the relationship of gastroesophageal reflux (GER) and respiratory effort. The present invention allows these measurements to be taken simultaneously and with the use of a single catheter. The present invention eliminates the need for a separate catheter and for the attachment of sensors to the body. In addition, the catheter of the present invention is of such a small diameter that it should not disturb normal sleep or other bed activity. As such, the present invention allows the effective study and analysis of sleep apnea that has heretofore eluded medical science.

The embodiment illustrated and discussed in the specification is intended only to teach those skilled in the art the best way known by the inventor to make and use the invention. Nothing in the specification should be considered as limiting the scope of the present invention. Any changes could be made by those skilled in the art to produce equivalent systems without departing from the invention. The present invention should only be limited by the following claims and their legal equivalents.

I claim:

1. An intraesophageal catheter comprising:
   a tubular body with an open and closed end;
   a pH sensor means extending through the interior of said tubular body for pH measurements;
   a balloon molded to the exterior surface of said exterior body, said balloon comprised of latex material, said balloon having a length of approximately four centimeters and an inflated outer diameter of approximately 8.4 millimeters;
   and a balloon inflation channel extending through the interior of said tubular body such that said balloon inflation channel pneumatically communicates with the interior of said balloon through a plurality of ports extending through said tubular body.

2. The catheter of claim 1, said balloon inflation channel being TEFLON lined, said balloon inflation channel having a female lure lock at the open end of said tubular body.

3. A method of measuring intraesophageal pH and air pressure comprising the steps of:
   inserting an intraesophageal catheter into the nose of a person, said intraesophageal catheter having a pH measurement head at the inserted end and a balloon inflation pressure sensor longitudinally displaced from said pH measurement head on said catheter;
   moving said intraesophageal catheter into the esophagus proximal to the stomach of said person;
   connecting said pH measurement head to an electric pH recorder exterior of said patient;
   inflating said balloon inflation pressure sensor such that said balloon inflation pressure sensor expands and contracts with the respiratory effort of said person;
   connecting said balloon inflation pressure sensor into a pneumatic pressure recorder exterior of said person; and
   monitoring the pH and pressure measurements simultaneously during the sleep cycle of said person.

* * * * *